United States Patent [19]

White

[11] 4,250,893
[45] Feb. 17, 1981

[54] SAMPLE COLLECTION DEVICE

[75] Inventor: Fred K. White, Miami, Fla.

[73] Assignee: American Hospital Supply Corporation, Evanston, Ill.

[21] Appl. No.: 13,244

[22] Filed: Feb. 21, 1979

[51] Int. Cl.³ .............................................. A61B 5/14
[52] U.S. Cl. .................................... 128/765; 128/767; 73/425.6
[58] Field of Search .................. 128/763–768, 128/770, 771; 73/425.4 P, 426.6; 215/228, 316, 317

[56] References Cited

U.S. PATENT DOCUMENTS

| 2,722,257 | 11/1955 | Lockhart | 128/767 X |
| 3,181,529 | 5/1965 | Wilburn | 128/767 X |
| 3,592,245 | 7/1971 | Schneller | 215/228 X |
| 3,718,133 | 2/1973 | Perry et al. | 128/767 X |
| 3,796,542 | 3/1974 | Kline | 128/767 X |
| 3,809,068 | 5/1974 | Kosowsky | 128/767 X |
| 4,024,857 | 5/1977 | Blecher et al. | 128/763 |

FOREIGN PATENT DOCUMENTS

| 213056 | 2/1962 | Sweden | 128/767 |
| 947908 | 1/1964 | United Kingdom | 128/763 |

Primary Examiner—Kyle L. Howell
Attorney, Agent, or Firm—Tilton, Fallon, Lungmus & Chestnut

[57] ABSTRACT

A device for collecting samples of blood and other fluides for clinical testing purposes. The device includes a deformable vial, a non-vented cap removably secured to the open end of the vial, such cap having a bevel-tipped collection tube extending therefrom, and a closure member for initially sealing the collection tube and, following the collection of a sample, the vial itself.

11 Claims, 5 Drawing Figures

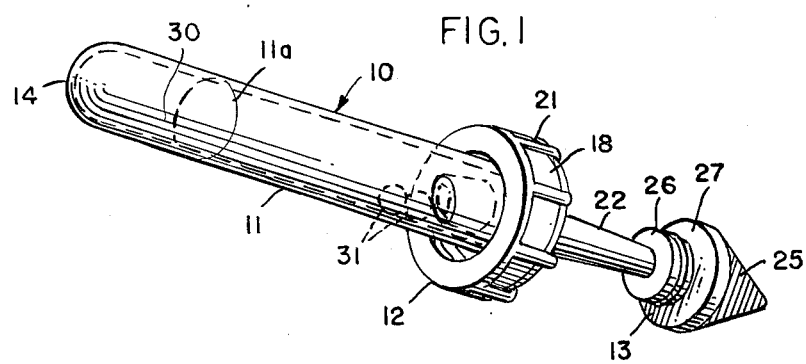
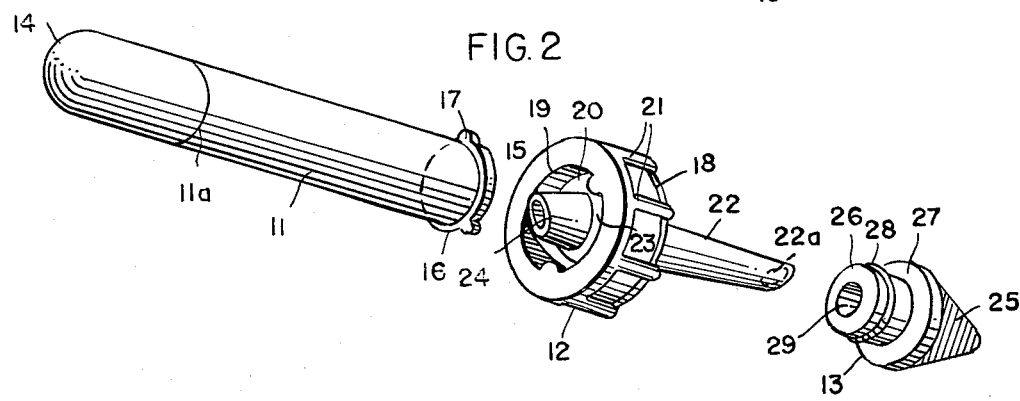
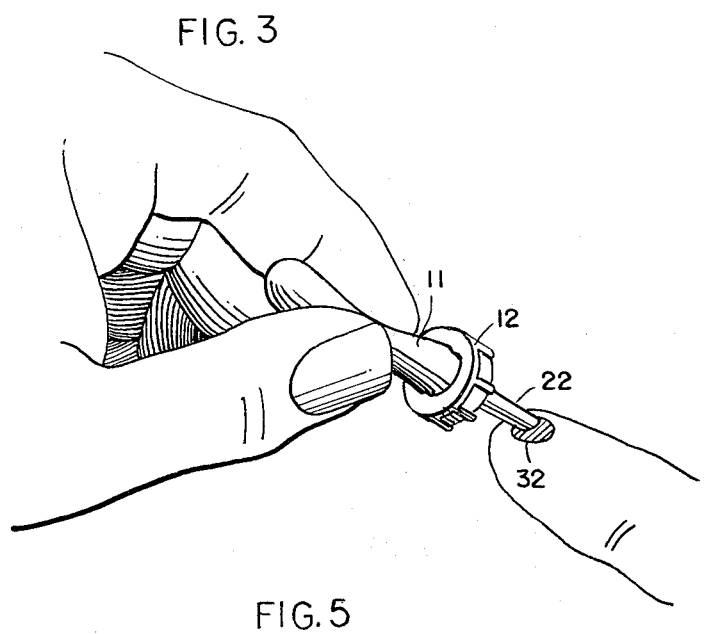
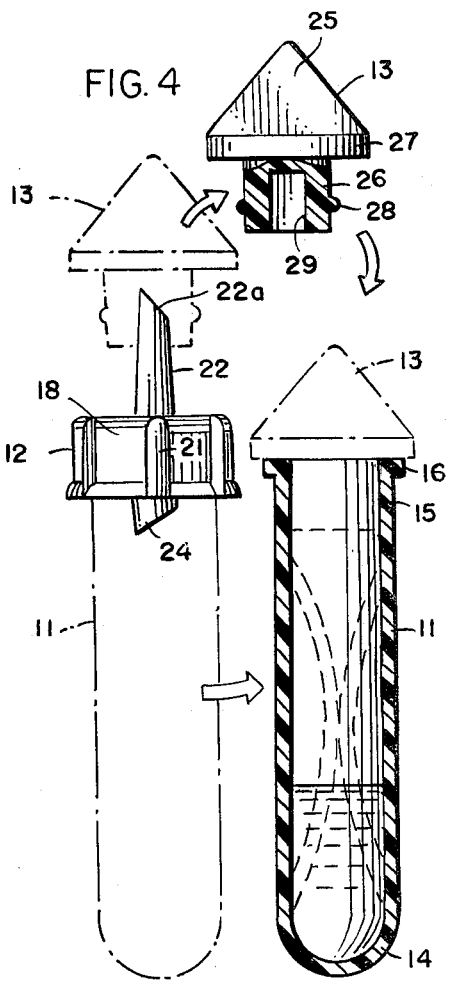
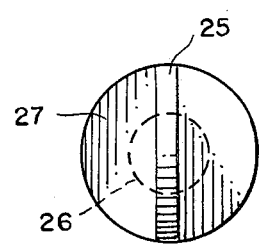

SAMPLE COLLECTION DEVICE

BACKGROUND OF THE INVENTION

U.S. Pat. No. 4,024,857 discloses a device for collecting a small quantity of capillary blood from a puncture site in the ear, finger, or other portion of a patient's body. Since the anticoagulated blood so collected and stored may then be used for microhematological procedures which by general definition involve quantities of 100 microliters ($\mu$l) or less, the device is disclosed and generally marketed as a micro blood collector. It consists essentially of a vial of rigid polymeric material, a vented cap which has a capillary tube for drawing the blood sample by gravity into the vial, and in the commercial form, a plug to replace the cap for the purpose of sealing the vial after a blood sample has been taken.

Replacement of the cap by the plug is essential if the vial is to be sealed because, in addition to providing a capillary tube, the cap is also vented. The vent is in turn required in order to allow the escape of air as the vial is filled with blood under the influence of gravity and capillary action. Therefore, following the drawing of a sample, a user must replace the cap with the plug in order to mix the sample with anticoagulant already present in the vial and to prevent contamination or loss of the contents of the vial during subsequent storage and handling.

As a practical matter, even further manipulation is required because of the need or desirability for supplying such a vial to the user in sealed condition. Such a vial is ordinarily supplied with a measured quantity of anticoagulant and one or more mixing beads and, to protect such contents, the vial is prefitted with the replacement plug. Thus, as part of the manipulative procedure, the user must first remove the plug and substitute the capillary cap and then, after the sample is drawn, remove the cap and replace the plug. Such manipulative steps are cumbersome, timeconsuming, and clearly undesirable not only because they increase the risks of contamination of the blood sample but also because they increase the chances that the user might accidentally touch the blood sample and become contaminated by pathogens in that sample.

Other patents indicating the state of the art are U.S. Pat. Nos. 3,902,477, 3,181,529, 3,513,829, 3,718,133, 3,322,114, and 2,655,152.

SUMMARY OF THE INVENTION

This invention is concerned with an improved micro collection device which is relatively simple, fast, and safe to use, and which therefore overcomes many of the shortcomings of prior devices described above. More specifically, it is an object of this invention to provide an improved blood collection device which does not require an interchange of plug and cap prior to the drawing of a sample, and does not even necessite such an interchange following the taking of a sample. No replacement of the cap is necessary for mixing the sample with anticoagulant, or for sealing the mixed sample for subsequent transportation or storage.

In brief, the device includes a flexible plastic vial having a pliable tubular body capable of being deformed by finger pressure and of recovering its original configuration upon removal of such force. A ventless cap is removably secured to the open end of the body, the cap having a narrow elongated collection tube projecting outwardly therefrom. A closure member is fitted upon the free end of the collection tube, the closure member having an integral handle and having a sleeve portion with a recess for sealingly but removably receiving the tip of the collection tube. In addition, the outer dimensions of the sleeve allow the sleeve to function as a plug for selectively sealing the vial should the collection cap be removed. An integral shield portion is interposed between the sleeve and handle portions of the closure member to protect the user against direct contact with the sample during attachment and detachment of the closure member and to provide a stop for limiting the extent of insertion of the sleeve portion into the neck of the vial.

Other features, objects, and advantages of the invention will become apparent from the specification and drawings.

DRAWINGS

FIG. 1 is a perspective view of the micro collection device of this invention.

FIG. 2 is an exploded perspective view showing the vial, cap, and closure member in separated condition for purposes of illustration.

FIG. 3 illustrates the method of use of the device in drawing a sample of blood.

FIG. 4 is a composite side elevational view, taken partly in section, of the components of the device, illustrating the interrelationship between such components.

FIG. 5 is an end view of the closure member.

DESCRIPTION OF PREFERRED EMBODIMENT

Referring to the drawings, the numeral 10 generally designates a micro collection device comprising a vial 11, a cap 12, and a closure member 13. The vial takes the form of an elongated tubular body having a closed end 14 and an open end 15. A bead or outwardly-projecting annular flange 16 is provided at the open end, the bead including a plurality of circumferentially spaced outwardly-projecting lugs 17.

An important aspect of the vial is that it is flexible, the tubular wall of the body not only being capable of inward deformation under finger pressure until the inside surfaces engage each other (FIGS. 3 and 4), but also being capable of recovering its original configuration upon removal of such force. Such elastic recovery must of course be accompanied by the inflow of fluid (gas or liquid) to occupy the expanding volume of the vial; hence, upon release of compressive force, the vial acts as a suction device useful in drawing a sample of blood or other liquid into the vial.

While the dimensions of the vial may be varied somewhat, it is apparent that the vial must be large enough to draw an adequate volume of liquid without excessive "milking", and preferably in a single compression-expansion cycle, and be small enough to be comfortably squeezed between the fingers as generally indicated in FIG. 3. A sample volume, which is only a portion of the total volume of the vial, should fall within the general range of 100 to 800 $\mu$l, the preferred range being about 200 to 600 $\mu$l. To achieve such sample-drawing capacity in a device capable of being readily manipulated by the fingers, it has been found that a tubular body of the generally cylindrical configuration shown should have a length within the range of about 30 to 60 millimeters (mm) and a diameter of approximately 5 to 20 mm. Such dimensions assume a wall thickness within the broad range of 0.2 to 0.8 mm, it being understood that the particular wall thickness selected depends in part on the resilience and modulus of the particular material selected. Any of a variety of flexible plastic materials may be selected although particularly effective results have been obtained using a polyolefin such as polypropylene. Whatever the selection, the material should have sufficient clarity so that the wall of the vial is generally transparent. As used herein, the term "transparent" is intended to include any material having sufficient clarity to permit the contents of the vial to be viewed through the wall of that vial; hence, milky, tinted, or even translucent materials may be suitable for that purpose.

Cap 12 includes a cup-shaped body portion 18 defining a cavity 19 for receiving the end portion 15 of the vial. Internal threads 20 are engagable with lugs 17 to permit the cap to be screwed tightly upon the open end of the vial. External longitudinal ribs 21 may be provided as shown to assist a user in gripping the cap for tightening as well as for attachment and detachment.

An elongated collection tube 22 projects outwardly and axially from the end wall 23 of the cap, the collection tube preferably having a beveled tip 22a as shown most clearly in FIG. 4. The lumen of the collection tube extends through the end wall of the cap and, in the embodiment depicted in the drawings, a tubular extension 24 projects into and beyond the cavity 19 of the cap to direct the flow of fluid into vial 11. Like the collection tube 22, extension 24 is coaxial with the remainder of the cap and may be beveled at its free end. Ideally, the collection tube and its extension are formed integrally with the other portions of the cap, although the parts might be formed separately and later fused or otherwise sealed together. In any event, the final result is a unitary cap which is ventless; that is, has no opening except for the lumen of the collection tube and its extension.

Closure member 13 includes a handle portion 25, a sleeve portion 26, and a shield portion 27. As shown most clearly in FIGS. 2 and 4, the sleeve portion is generally cylindrical and has an external annular rib 28 dimensioned to make fluid-tight sealing contact with the inner surface of vial 11 at the mouth end thereof. The sleeve also has an axial recess 29 for snugly and sealingly receiving the tip portion 22a of tapered collection tube 22. Thus, when the tip of the collection tube is inserted into the blind recess 29 as shown in FIGS. 1 and 4, the contents of the vial are sealed against escape and against contact with contaminants that might otherwise enter through the bore of the cap. If desired, the recess of the sleeve may be tapered; in any event, at least one of the coacting surfaces (i.e., the outer surface of the collection tube or the inner surface of the recess) should be tapered to insure a fluid-tight seal when the parts are fitted together.

Handle portion 25 takes the form of a wing-like tab disposed in a longitudinal and diametrical plane disposed at the end of the closure member opposite from sleeve portion 26. In outline, the handle tab is triangular in configuration, although other shapes may be utilized. The thin planar configuration of the handle portion is important because it permits that portion to be grasped between a user's thumb and index finger with such fingers protected by shield portion 27.

The shield portion 27 is interposed between the handle and sleeve portion of the closure member and is generally disk-shaped. The diameter of the shield portion is substantially greater than the outside diameter of sleeve portion 26 and, as shown in FIG. 4, is even larger than the maximum outside diameter of vial 11. The entire closure member may be integrally formed from any suitable polymer or other material capable of forming a fluid-tight seal not only with the collection tube 22 but also directly with vial 11. Effective results have been achieved by forming the closure member from essentially the same polyolefin (polypropylene or polyethylene) used for the vial and cap.

The micro collection device 10 is supplied to the user in the sealed condition illustrated in FIG. 1. An anticoagulant 30 may be sealed within the vial in powdered, tableted, or liquid form and, in that event, one or more inert beads 31 of ceramic, plastic, or other suitable material may be disposed within the vial to assist in mixing the anticoagulant with a drawn sample of blood. Such sample is drawn simply by removing closure 13, squeezing the vial and then, after the tip of the collection tube has been introduced into blood 32 at the puncture site, releasing the compressive force on the sides of the vial to draw a quantity of blood into the vial. During the sample-taking step, the user may find it expedient to hold the closure member 13 with the same hand used to remove it from collection tube 22, gripping the handle tab 25 between his thumb and index fingers, so that the closure member may be replaced upon the collection tube immediately after the sample is taken in the manner depicted in FIG. 3. In other words, once a flow of blood has developed at the puncture site, the user may without changing the position of his hands on the components of the device perform the steps of removing the closure member 13 from the collection tube, drawing the blood sample as depicted in FIG. 3, and then replacing the closure member upon the collection tube to reseal the container. When so resealed, the device may be gently agitated to insure thorough mixing of the blood sample and the anticoagulant.

In some cases a user may prefer to remove cap 12 from vial 11 either before or after the mixing step. In that event, the cap may be unscrewed from the mouth of the vial and discarded, and the closure member may be fitted in place to seal the vial as shown in the right hand portion of FIG. 4.

To assist a user in drawing an adequate quantity of blood for the various clinical determinations to be made (white blood count, red blood count, white cell differential, mean corpuscular hemoglobin, etc.) a calibration or index mark 11a may be provided on the side wall of vial 11. Precision in filling the vial to the mark is not required; however, substantial underfill should be avoided because of possible insufficiency in sample quantity for the intended clinical determinations, and substantial overfill should also be avoided because the amount of anticoagulant 30 may be insufficient for an excessive sample. The vial 11 is generally dimensioned so that the volume of sample represented by the index mark will be approximately drawn when the vial is squeezed and released once in the manner shown in FIGS. 3 and 4. Stated differently, the volume reduction which occurs when the vial is compressed or squeezed as represented by broken lines in the right hand view of FIG. 4 corresponds generally to the volume below the index mark when the vial is in an undeformed state.

While in the foregoing I have disclosed an embodiment of the invention in considerable detail for purposes of illustration, it will be understood by those skilled in the art that many of these details may be varied without departing from the spirit and scope of the invention.

I claim:

1. A device for use in collecting fluid samples for laboratory use, comprising a flexible plastic vial having a pliable tubular body capable of being deformed by finger pressure and of recovering its original configuration upon removal of such force; said body having an opening at one end thereof; a ventless cap sealingly but removably secured to said body at said opening; said cap having a narrow elongated collection tube projecting outwardly therefrom; and a closure member having an integral handle portion and a sleeve portion at opposite ends thereof; said sleeve portion having a recess-defining inner surface removably receiving and sealingly engaging the free end of said collection tube and having an outer surface dimensioned to be sealingly received within the opening of said vial when said cap is removed and replaced by said closure member, said cap including an inner tube disposed within said vial and constituting an inner extension of said collection tube.

2. The device of claim 1 in which said inner tube is coaxial with said vial and has a beveled free end.

3. The device of claim 2 in which said vial is substantially transparent.

4. A device for use in collecting fluid samples for laboratory use, comprising a flexible plastic vial having a pliable tubular body capable of being deformed by finger pressure and of recovering its original configuration upon removal of such force; said body having an opening at one end thereof; a ventless cap sealingly but removably secured to said body at said opening; said cap having a narrow elongated collection tube projecting outwardly therefrom; and a closure member having an integral handle portion and a sleeve portion at opposite ends thereof, and having a transverse and generally disk-shaped shield portion interposed between said handle and sleeve portions; said sleeve portion having a recess-defining inner surface removably receiving and sealingly engaging the free end of said collection tube and having an outer surface dimensioned to be sealingly received within the opening of said vial when said cap is removed and replaced by said closure member; said shield portion having a diameter substantially larger than the outside diameter of said sleeve portion.

5. The device of claim 4 in which said shield portion has a diameter which is also larger than the outside diameter of said vial adjacent said opening.

6. The device of claim 4 in which said handle portion comprises a thin planar tab disposed in an axially and diametrically extending plane relative to said disk-shaped shield portion.

7. The device of claims 3, 5, or 6 in which said handle, shield, and sleeve portions are formed integrally of flexible plastic material.

8. The device of claim 3 in which said body has a length within the range of 30 to 60 millimeters and a diameter within the range of 5 to 20 millimeters.

9. The device of claim 4 in which said cap also includes an inner tube disposed within said vial and constituting an inner extension of said collection tube.

10. The device of claim 9 in which said inner tube has a beveled free end.

11. The device of claim 4 in which said vial is substantially transparent.

* * * * *